(12) United States Patent
Miura et al.

(10) Patent No.: US 9,645,021 B2
(45) Date of Patent: May 9, 2017

(54) SHEET PRESSURE SENSOR (71) Applicant: Nissan Motor Co., Ltd., Kanagawa (JP)

(72) Inventors: Hiroaki Miura, Kanagawa (JP); Takashi Sunda, Kanagawa (JP); Yasuhiro Fukuyama, Kanagawa (JP)

(73) Assignee: NISSAN MOTOR CO., LTD., Kanagawa (JP)

( * ) Notice: Subject to any disclaimer, the term of this patent is extended or adjusted under 35 U.S.C. 154(b) by 183 days.

(21) Appl. No.: 14/378,271

(22) PCT Filed: Feb. 12, 2013

(86) PCT No.: PCT/JP2013/053216
§ 371 (c)(1),
(2) Date: Aug. 12, 2014

(87) PCT Pub. No.: WO2013/122038
PCT Pub. Date: Aug. 22, 2013

(65) Prior Publication Data
US 2015/0000425 A1  Jan. 1, 2015

(30) Foreign Application Priority Data
Feb. 13, 2012  (JP) ................................ 2012/028118

(51) Int. Cl.
*G01L 1/22* (2006.01)
*G01L 1/20* (2006.01)
(Continued)

(52) U.S. Cl.
CPC ................ *G01L 1/22* (2013.01); *G01L 1/205* (2013.01); *A61B 5/1115* (2013.01);
(Continued)

(58) Field of Classification Search
None
See application file for complete search history.

(56) References Cited

U.S. PATENT DOCUMENTS 4,659,873 A * 4/1987 Gibson .................. H01H 3/141
178/18.05
6,277,771 B1 * 8/2001 Nishimura .............. B29C 70/22
324/71.1
(Continued)

FOREIGN PATENT DOCUMENTS

CN        1429394 A       7/2003
FR  WO 2012095608 A2 *  7/2012  ............... G01L 1/18
(Continued)

OTHER PUBLICATIONS

International Search Report issued in PCT/JP2013/053216 mailed on Mar. 19, 2013 (4 pages).

*Primary Examiner* — Jill Culler
(74) *Attorney, Agent, or Firm* — Osha Liang LLP (57) ABSTRACT

A sheet pressure sensor includes a first fiber layer, a second fiber layer, and a third fiber layer provided between the first and second fiber layers. The third fiber layer has connecting yarns that electrically connect first conductive portions of the first fiber layer and the second conductive portion in the second fiber layer with a predetermined electric resistivity. The sheet pressure sensor further includes a measuring instrument for measuring electric resistance between at least one of the first conductive portions and the second conductive portion. The connecting yarns unstrain due to deformation of the first or second conductive portion which is generated by applied pressure, and then are short-circuited with one of them. The sheet pressure sensor can detect the pressure while keeping air ventilation characteristic by giving a pressure detection function to the fiber layers.

9 Claims, 8 Drawing Sheets (51) Int. Cl.
*A61B 5/00* (2006.01)
*A61B 5/11* (2006.01)
*B60N 2/02* (2006.01)

(52) U.S. Cl.
CPC ........... *A61B 5/6891* (2013.01); *A61B 5/6893* (2013.01); *A61B 2562/0247* (2013.01); *A61B 2562/046* (2013.01); *A61B 2562/16* (2013.01); *B60N 2002/0272* (2013.01)

(56) References Cited

U.S. PATENT DOCUMENTS

| | | | | |
|---|---|---|---|---|
| 6,333,736 | B1* | 12/2001 | Sandbach | G06F 3/0414 178/18.03 |
| 6,493,933 | B1* | 12/2002 | Post | H01L 23/4985 257/E23.065 |
| 7,145,432 | B2 | 12/2006 | Lussey et al. | |
| 7,161,084 | B2* | 1/2007 | Sandbach | G06F 3/023 174/117 M |
| 7,301,435 | B2 | 11/2007 | Lussey et al. | |
| 7,377,133 | B2* | 5/2008 | Sandbach | H01H 3/141 66/170 |
| 7,750,790 | B2* | 7/2010 | Yang | G01L 1/22 338/114 |
| 8,089,336 | B2* | 1/2012 | Burkitt | G06F 3/0202 338/101 |

FOREIGN PATENT DOCUMENTS

| | | |
|---|---|---|
| JP | 2-304824 A | 12/1990 |
| JP | H06-274265 A | 9/1994 |
| JP | 2010-014694 A | 1/2010 |
| JP | 2010-101827 A | 5/2010 |
| WO | 01/88935 A1 | 11/2001 |
| WO | 2005/031557 A1 | 4/2005 |

\* cited by examiner

| | Conductive Polymer Fiber in Variable Resistor Layer | | | Upper and Lower Layers | | | | Evaluation Result | |
|---|---|---|---|---|---|---|---|---|---|
| | | | | Upper Layer | | Lower Layer | | | |
| | Conductive Material | Cross-sectional Pattern of Fiber | Resistivity [Ω·cm] | Conductive Material | Pattern | Conductive Material | Pattern | Resistance [Ω] | Air Ventilation Volume [cc/(cm²·sec)] |
| 1st Embodiment | PEDOT/PSS | Uniform | 0.1 | Ag-Coated Fiber | Lateral Stripe | Ag-Coated Fiber | Unpatterned | 0.5 ~ 5 | 225 |
| 2st Embodiment | PEDOT/PSS | Uniform | 0.1 | Ag-Coated Fiber | Lateral Stripe | Ag Paste | Vertical Stripe | 9 ~ 112 | 220 |
| 3st Embodiment | Carbon Black | Coated | 100 | Ag-Coated Fiber | Lateral Stripe | Ag-Coated Fiber | Unpatterned | 48 ~ 212 | 253 |
| 4st Embodiment | Ag | Coated | 0.01 | Ag-Coated Fiber | Lateral Stripe | Ag-Coated Fiber | Unpatterned | 0.03 ~ 0.10 | 244 |
| 5st Embodiment | ZnO | Coated | 10 | Ag-Coated Fiber | Lateral Stripe | Ag-Coated Fiber | Unpatterned | 6 ~ 32 | 248 |
| 6st Embodiment | PEDOT/PSS | Coated | 1 | Ag-Coated Fiber | Lateral Stripe | Ag-Coated Fiber | Unpatterned | 1.1 ~ 17 | 268 |
| 7st Embodiment | Polypyrrol | Uniform | 1 | Ag-Coated Fiber | Lateral Stripe | Ag-Coated Fiber | Unpatterned | 0.8 ~ 13 | 242 |
| 1st Comparison Example | Conductive Rubber (with Holes) | — | 5 | Ag-Coated Fiber | Lateral Stripe | Ag-Coated Fiber | Unpatterned | 0.02 ~ 0.08 | (Unmesurable) |
| 2st Comparison Example | Conductive Rubber (w/o Holes) | — | 5 | Ag-Coated Fiber | Lateral Stripe | Ag-Coated Fiber | Unpatterned | (Unmesurable) | 206 |

SHEET PRESSURE SENSOR

BACKGROUND

Technical Field

The present invention relates to a sheet pressure sensor that can measure pressure at plural positions Related Art A Patent Literature 1 listed below discloses a sheet input device using a pressure-sensitive conductive rubber as a sheet pressure sensor. The sheet input device includes a three-layered structure in which the sheet-shaped pressure-sensitive conductive rubber is sandwiched between a pair of polyester sheets, and the conductive rubber sheet deforms when pressure is applied to one of the polyester sheets to reduce electric resistance of the conductive rubber sheet. A pressure change is measured based on this change of the electric resistance.

CITATION LIST

Patent Literature

Patent Literature 1: Japanese Unexamined Patent Publication No. H6-274265 (FIG. 1)

SUMMARY OF INVENTION

In a case where the above-explained pressure sensor (sheet input device) is used for an outer layer (at a position contacted with a human body or a position near a human body) such as a seat for an automobile and bedclothes in order to measure pressure distribution due to a human body or to judge seating on a seat, comfortability degrades due to heat and humidity or the like, because the conductive rubber sheet doesn't possesses air ventilation characteristic. In addition, in a case where air ventilation characteristic is given by holes provided on the conductive rubber sheet, stiffness near the holes reduces and thereby it becomes deformed easily. Therefore, a deformed amount at positions near the holes becomes different from that at other positions when pressure is applied, so that the deformation of the conductive rubber sheet becomes complex and measurement of a pressure change becomes difficult.

One or more embodiments of the present invention provides a sheet pressure sensor that can detects pressure while keeping air ventilation characteristic by giving a pressure detection function to a fiber layer.

An aspect of the present invention provides a sheet pressure sensor comprising: a first fiber layer; a second fiber layer that is disposed oppositely to the first fiber layer and distanced away from the first fiber layer; and a third fiber layer that is provided between the first fiber layer and the second fiber layer, wherein the first fiber layer has a plurality of first conductive portions having conductivity, and a plurality of first non-conductive portions electrically insulating the plurality of first conductive portions, respectively, the second fiber layer has a second conductive portion having conductivity; the third fiber layer has a plurality of connecting yarns that is extended from one of the plurality of first conductive portions and the second conductive portion to another thereof to electrically connect the plurality of first conductive portions and the second conductive portion with a predetermined electric resistivity, the sheet pressure sensor further comprises a measuring instrument for measuring electric resistance between at least one of the plurality of first conductive portions and the second conductive portion, and the plurality of connecting yarns unstrains due to deformation of the at least one of the plurality of first conductive portions or the second conductive portion to be short-circuited with the at least one of the plurality of first conductive portions or the second conductive portion, the deformation being generated by application of pressure.

DETAILED DESCRIPTION

Figure 1:
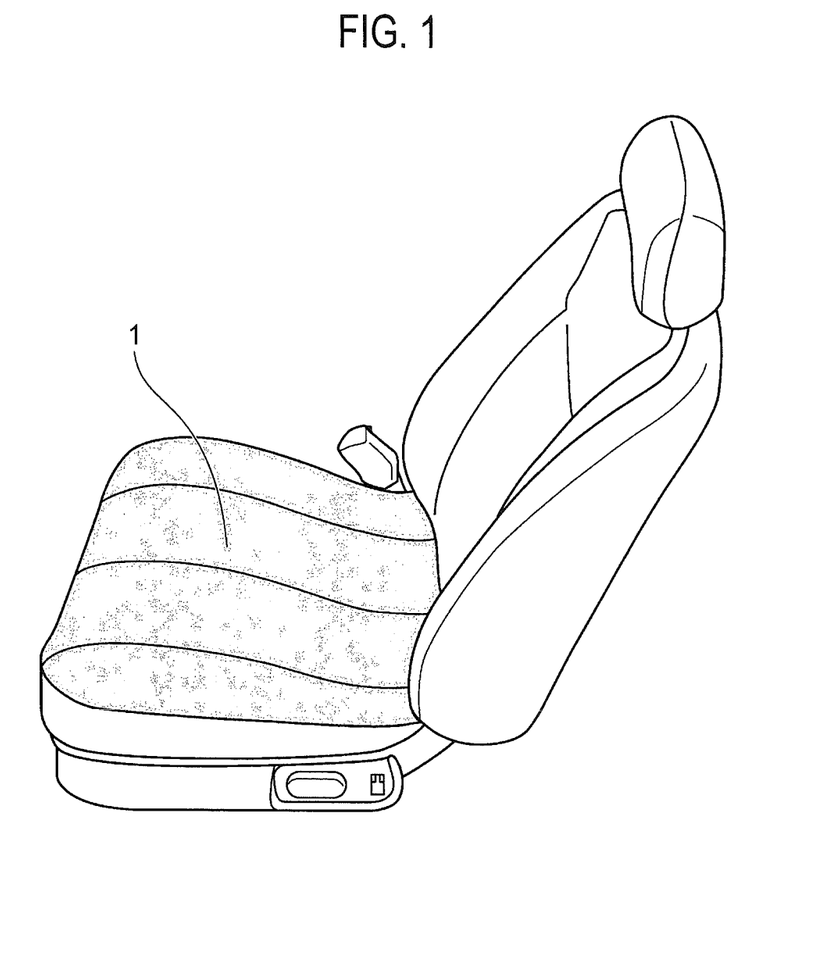
FIG. 1 is a perspective view showing an entire of a seat including a sheet pressure sensor according to a first or second embodiment on its seating face.

Hereinafter, embodiments of a sheet pressure sensor will be explained with reference to the drawings. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention. In the following embodiments, the sheet pressure sensor is used as a pressure sensor of a seat for an automobile and provided on a seating face of the seat, as shown in FIG. 1.

Figure 2:
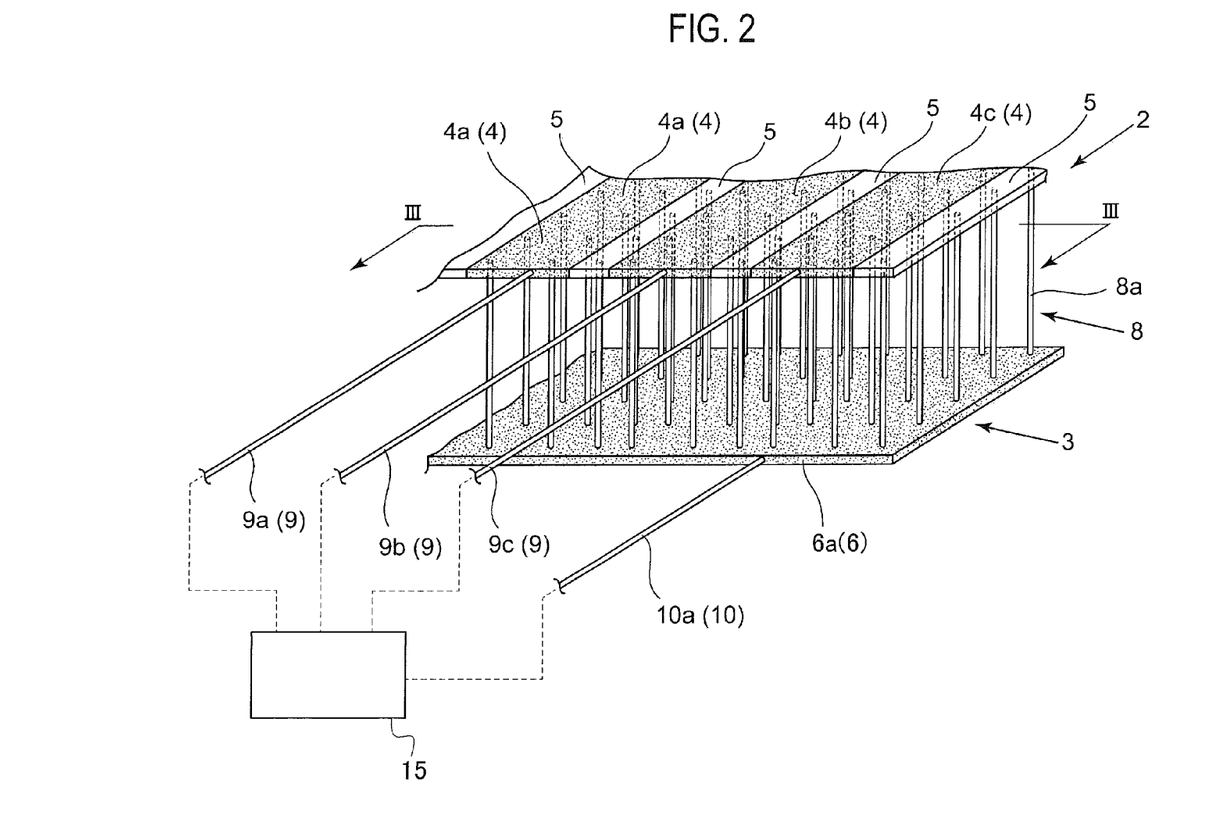
FIG. 2 is a schematic perspective view showing structure of the sheet pressure sensor according to the first embodiment.

As shown in FIG. 2, a sheet pressure sensor 1 according to a first embodiment includes a three-layered structure composed of an upper layer 2 (corresponding to a first fiber layer in one or more embodiments of the present invention), a lower layer 3 (corresponding to a second fiber layer in one or more embodiments of the present invention), and a variable resistor layer 8 (corresponding to a third fiber layer in one or more embodiments of the present invention). The upper layer 2 is configured by aligning upper layer conductive portions 4 (corresponding to first conductive portions in one or more embodiments of the present invention) and upper layer non-conductive portions 5 (corresponding to first non-conductive portions in one or more embodiments of the present invention) alternately. Note that the upper layer conductive portions 4 and the upper layer non-conductive portions 5 are woven continuously while fibers constituting them are changed over.

Each of the upper layer conductive portions 4 (4a, 4b, 4c . . . ) is formed of silver-coated fibers (manufactured by Shaoxing Yunjia Textile Product Co., Ltd.) (width 10 mm and length 200 mm). Each of the upper layer non-conductive portions 5 is formed of non-conductive polyester fiber (manufactured by Central Fiber Materials Ltd.: Gunze Polina) (with 2 mm and length 200 mm). The lower layer 3 is formed of a lower layer conductive portion 6 (6a) made by weaving silver-coated fibers (manufactured by Shaoxing Yunjia Textile Product Co., Ltd.) into a sheet shape.

Figure 3:
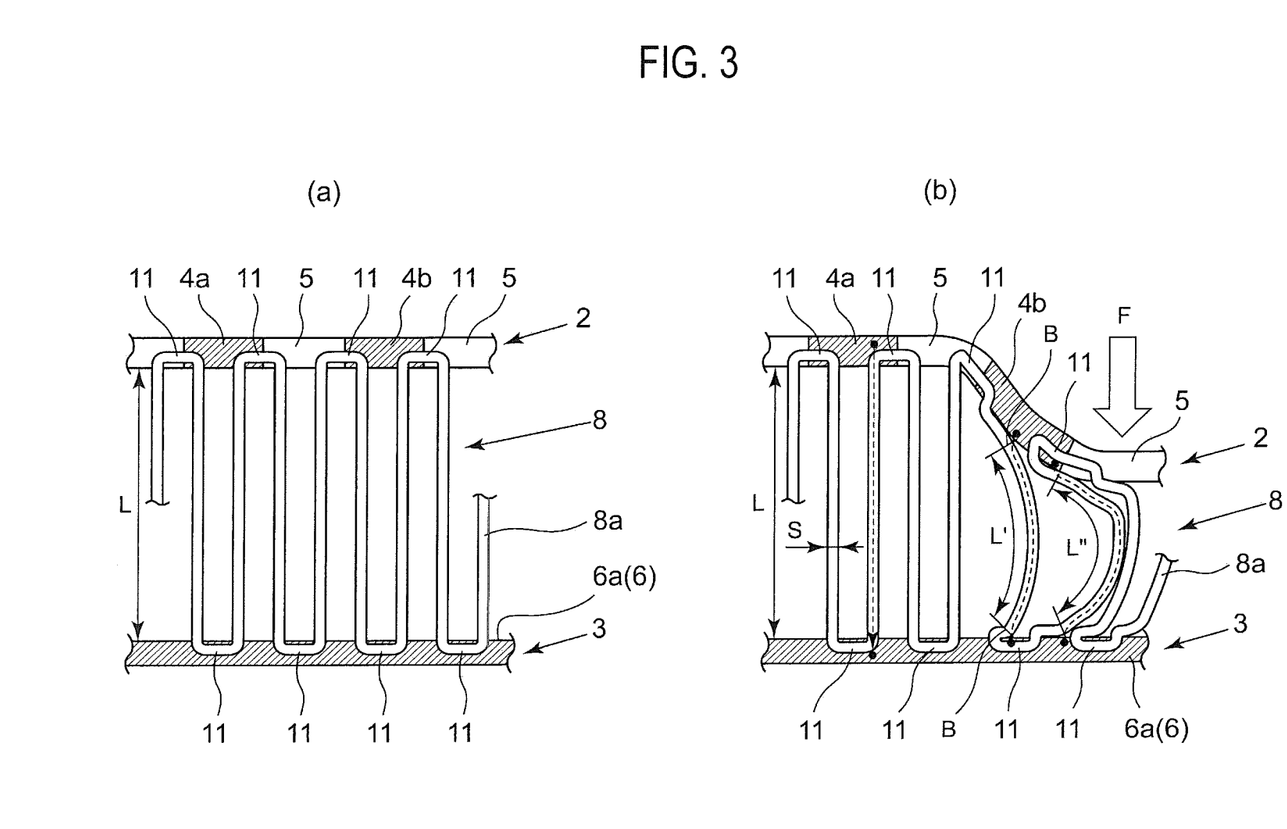
FIG. 3 is a cross-sectional view taken along a line III-III shown in FIG. 2, and (a) shows a state before pressure is applied and (b) shows a state while pressure is applied.

As shown in FIG. 3(a), the variable resistor layer 8 is formed of connecting yarns 8a extended up and down so as to connect the upper layer conductive portions 4 and the lower layer conductive portion 6 with each other electrically. The connecting yarn(s) 8a is a conductive polymer fiber that is made by a wet-spinning method and has an about 10 μm diameter. Namely, the connecting yarn(s) 8a (the conductive polymer fiber(s)) is extended from one of the upper layer conductive portion(s) 4 and the lower layer conductive portion 6 to another of them. The connecting yarn(s) 8a is manufactured by using acetone (manufactured by WAKO-Chemicals: 019-00353) as a solvent phase and extruding a spinning dope made by mixing once-filtrated aqueous dispersion of conductive polymer PEDOT/PSS (manufactured by Heraeus GmbH: Clevious P) and 7 wt % aqueous solution of polyvinyl alcohol [PVA] (manufactured by Kanto Chemical Co., Inc.) from a micro syringe (manufactured by Ito Corporation: MS-GLL100, inner diameter 260 pin) by a flow speed 2 μl/min. Electric resistivity of this conductive polymer fiber is measured in compliance with JIS K 7194 (Testing method for resistivity of conductive plastics with a four-point probe array), and thereby the electric resistivity is about $10^{-1}$ Ω·cm.

Gauge, number of feeders and so on are adjusted so that thickness of the variable resistor layer 8 becomes 10 mm while weaving the connecting yarns 8a by using a circular knitting machine manufactured by Precision Fukuhara Works, Ltd. and proportion of the conductive polymer fibers in a unit area of an cross-sectional plane becomes 50% when cutting the variable resistor layer 8 in a plane parallel to the upper layer 2.

In addition, an upper layer wire 9a is electrically connected with the upper layer conductive portion 4a, an upper layer wire 9b is electrically connected with the upper layer conductive portion 4b, and an upper layer wire 9c is electrically connected with the upper layer conductive portion 4c. A lower layer wire 10a is electrically connected with the lower layer conductive portion 6. The upper layer wires 9 (9a, 9b, 9c . . . ) and the lower layer wire 10a are connected with a resistance measurement device 15 (a measuring instrument/measurement means in one or more embodiments of the present invention). The resistance measurement device 15 measures electric resistance between the upper layer wire 9a and the lower layer wire 10a, electric resistance between the upper layer wire 9b and the lower layer wire 10a, electric resistance between the upper layer wire 9c and the lower layer wire 10a, and so on.

A length L of the connecting yarn(s) 8a between the upper layer conductive portion 4a and the lower layer conductive portion 6a is indicated by an equation (1) shown below as a function of pressure F applied to the sheet pressure sensor 1. A coefficient α is an inverse number of a spring constant of the sheet pressure sensor 1 in its compression direction.

$$L = \alpha F \quad (1)$$

L: the length [mm] of the connecting yarn 8a, F: the pressure [Pa] applied to the sheet pressure sensor 1, and a: the coefficient [mm/Pa]

Here, the electric resistance R between the upper layer conductive portion 4a and the lower layer conductive portion 6a is indicated by an equation (2) shown below by using an electric resistivity ρ, the length L of the connecting yarn 8a and a cross-sectional area S of the connecting yarn 8a.

$$R = \rho L / S \quad (2)$$

R: the electric resistance [kΩ], ρ: the electric resistivity [Ω·cm], and S: the cross-sectional area [mm²]

Measurement of the pressure applied to the upper layer conductive portion(s) 4 (or the lower layer conductive portion 6) will be explained. When no pressure is applied to the upper layer conductive portion(s) 4, the connecting yarn(s) 8a between the upper layer conductive portion(s) 4 and the lower layer conductive portion 6 maintains its predetermined length L autonomously as shown in FIG. 3(a). When pressure F is applied to the upper layer conductive portion(s) 4, the upper layer conductive portion(s) 4 is curved downward (to a side of the lower layer conductive portion 6) and the connecting yarn(s) 8a connected with the upper layer conductive portion(s) 4 unstrains, so that the connecting yarn(s) 8a, and the upper layer conductive portion 4 and the lower layer conductive portion 6 are contacted at contact points B, respectively. At this time, a conducting path (shown by a dotted line in FIG. 3(b)) between the upper layer conductive portion 4 and the lower layer conductive portion 6 has a length L'. This length L' becomes shorter than the length L while the pressure F is not applied. In a case where the pressure F applied to the upper layer conductive portion 4 is higher, the upper layer conductive portion 4 is curved downward further, and the conducting path has a length L". This length L" becomes shorter than the above-explained length L'. Therefore, the electric resistance R between the upper layer conductive portion 4 and the lower layer conductive portion 6 bears a proportionate relationship to the (electrically-effective) length (L', L") of the connecting yarn 8a, and becomes smaller when the pressure F applied to the upper layer conductive portion 4 becomes higher.

Figure 4:
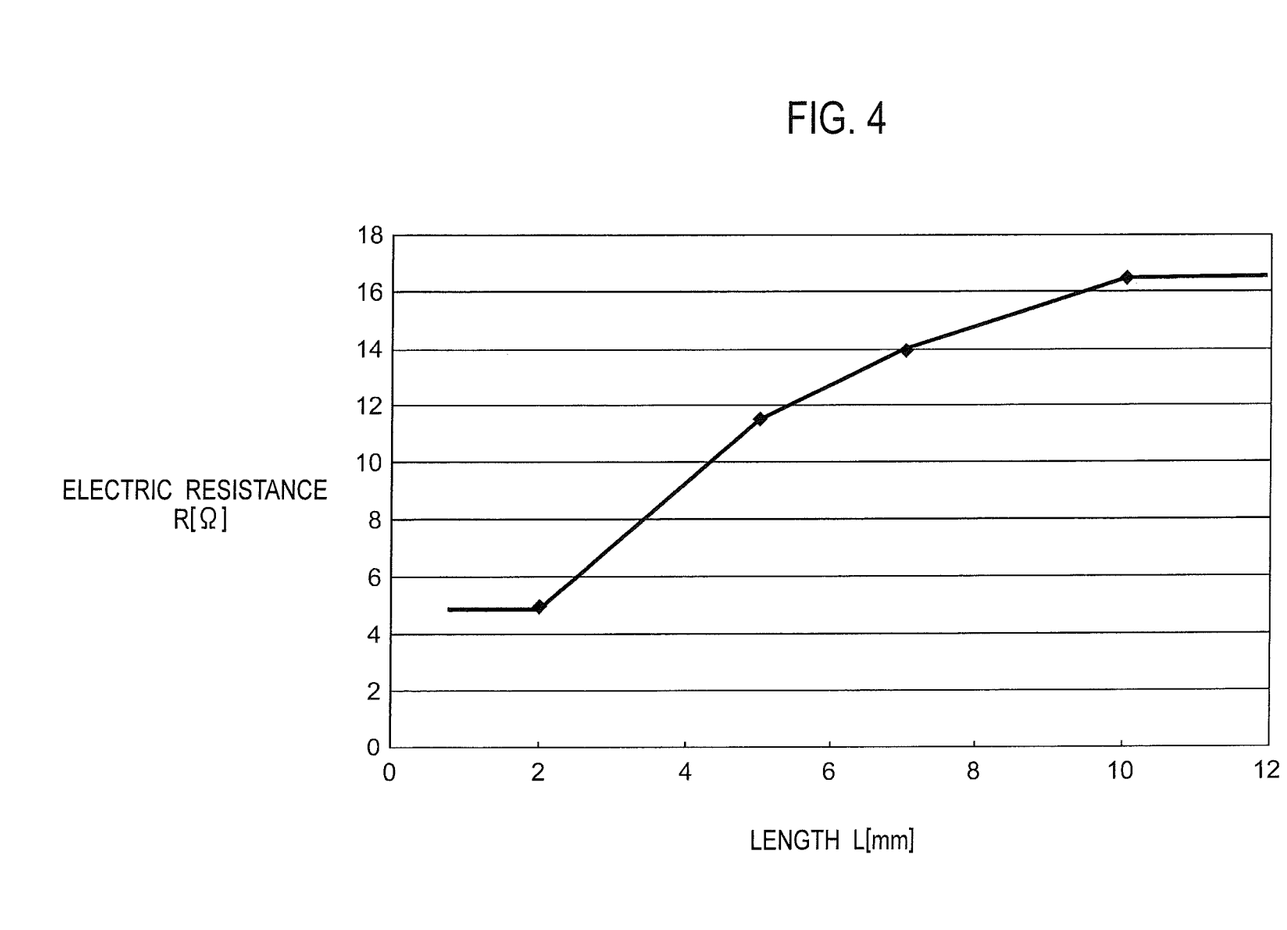
FIG. 4 is a graph showing an electric resistance change of the pressure sensor.

Therefore, the applied pressure F and the electric resistance R between the upper layer conductive portion 4 and the lower layer conductive portion 6 vary continuously as shown in FIG. 4. Thus, the pressure F can be calculated from the electric resistance R, and thereby the variable resistor layer 8 has a pressure detection function. Since the upper layer 2, the lower layer 3 and the variable resistor layer 8 have air ventilation characteristic and the variable resistor layer 8 has a pressure detection function as explained above, the sheet pressure sensor 1 can detect the pressure F applied to the upper layer conductive portion(s) 4 or the lower layer conductive portion 6 while keeping air ventilation characteristic. Here, it is impossible in the present embodiment to detect a position on the upper layer conductive portion 4a, 4b, 4c . . . along its longitudinal direction to which the pressure F is applied. According to a second embodiment to be explained next, it is possible to detect a position on the upper layer conductive portion 4a, 4b, 4c . . . along its longitudinal direction to which the pressure F is applied.

Figure 5:
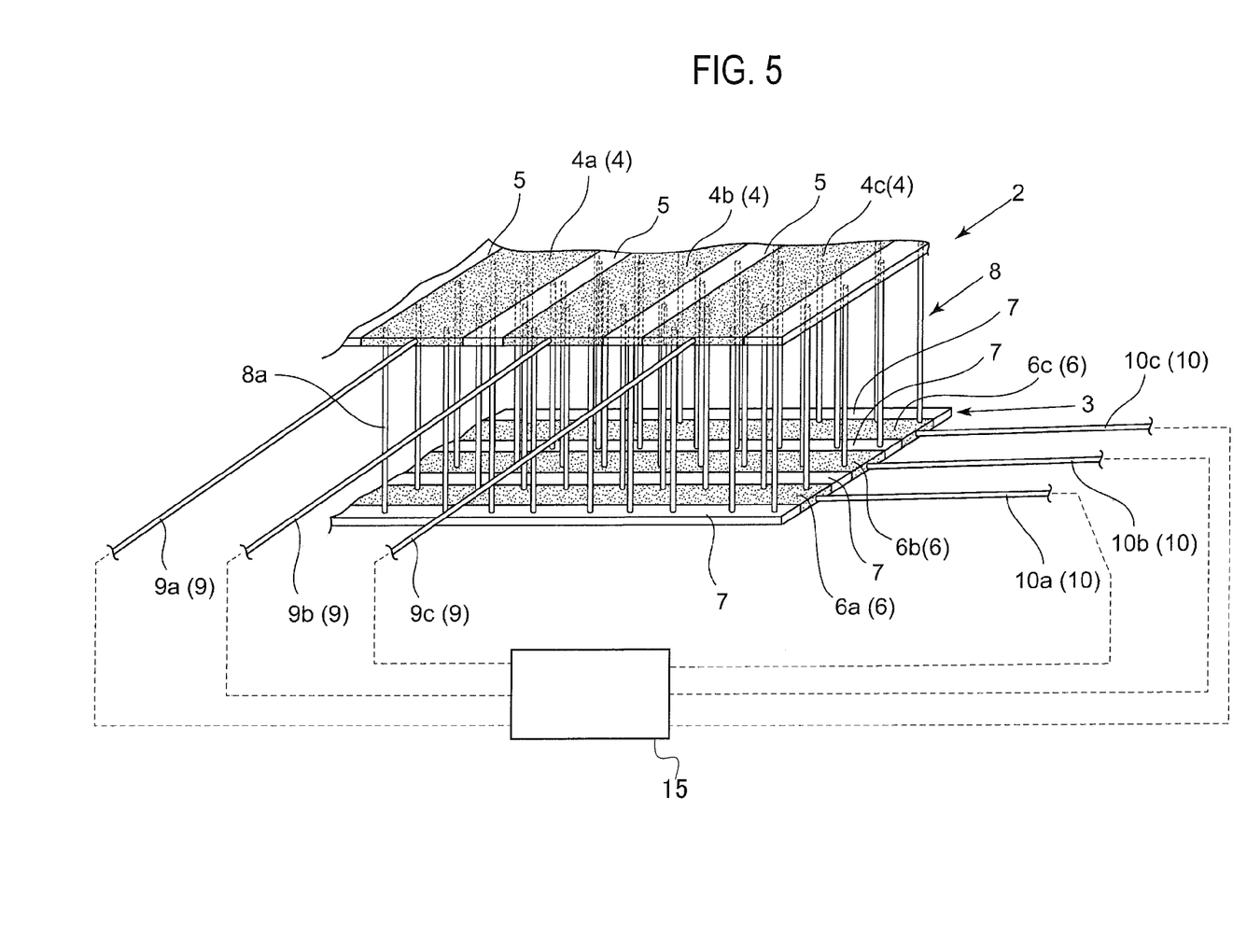
FIG. 5 is a schematic perspective view showing structure of the sheet pressure sensor according to the second embodiment.

As shown in FIG. 5, a sheet pressure sensor 1 according to the second embodiment includes a three-layered structure composed of an upper layer 2, a lower layer 3, and a variable resistor layer 8. However, in the sheet pressure sensor 1 according to the present embodiment, a structure of the lower layer 3 is different from the structure in the first embodiment, and thereby configuration for detecting pressure is also different. Hereinafter, an identical or equivalent component(s) is labelled with an identical reference number, and its redundant explanation will be omitted.

Similarly to the first embodiment, the upper layer 2 is configured by aligning the upper layer conductive portions 4 and the upper layer non-conductive portions 5 alternately. In the present embodiment, also the lower layer 3 is configured by aligning lower layer conductive portions 6 and lower layer non-conductive portions 7 alternately. Similarly to the first embodiment, the variable resistor layer 8 is formed of the connecting yarns 8a extended up and down so as to connect the upper layer conductive portions 4 and the lower layer conductive portions 6.

Configuration of the upper layer 2 (the upper layer conductive portions 4 and the upper layer non-conductive portions 5) is identical to that of the upper layer 2 in the first embodiment. On the other hand, the lower layer 3 is formed of polyester fibers. Each of the lower layer conductive portions 6 (6a, 6b, 6c . . . ) is formed by pasting conductive paste (manufactured by Fujikura Kasei Co., Ltd.: Dotite (registered trademark)) on the above-mentioned polyester fibers (width 200 mm and length 10 mm). The above-explained conductive paste is not pasted on the lower layer non-conductive portions 7 (width 200 mm and length 2 mm). The upper layer conductive portions 4 and the lower layer conductive portions 6 are arranged so as to cross with each other (almost perpendicular to each other in the present embodiment) when viewed from above (from a direction orthogonal to the sheet pressure sensor 1). Therefore, each of the lower layer conductive portions 6 is electrically connected with all the upper layer conductive portions 4 by the connecting yarns 8a.

A lower layer wire 10a is electrically connected with the lower layer conductive portion 6a, a lower layer wire 10b is electrically connected with the lower layer conductive portion 6b, and a lower layer wire 10c is electrically connected with the lower layer conductive portion 6c. The upper layer wires 9 and the lower layer wires 10 are connected with the resistance measurement device 15. The resistance measurement device 15 measures electric resistance between the upper layer wire 9a and the lower layer wire 10a, electric resistance between the upper layer wire 9b and the lower layer wire 10a, electric resistance between the upper layer wire 9c and the lower layer wire 10a, and so on. Similarly, the resistance measurement device 15 measures electric resistance between the upper layer wire 9a and the lower layer wire 10b, electric resistance between the upper layer wire 9b and the lower layer wire 10b, electric resistance between the upper layer wire 9c and the lower layer wire 10b, and so on. Hereinafter, the same applies to the lower layer wire 10c and so on.

Measurement of the pressure applied to the upper layer conductive portion 4a (or the lower layer conductive portion 6a) will be explained. When no pressure is applied to the upper layer conductive portion 4a, the connecting yarn(s) 8a between the upper layer conductive portion 4a and the lower layer conductive portion 6a (similarly to the lower layer conductive portion 6b or 6c) maintains its predetermined length L autonomously as shown in FIG. 3(a). When pressure F is applied to the upper layer conductive portion(s) 4, the upper layer conductive portion(s) 4 is curved downward (to a side of the lower layer conductive portions 6) and the connecting yarn(s) 8a connected with the upper layer conductive portion(s) 4 unstrains, so that the connecting yarn(s) 8a, and the upper layer conductive portion 4 and the lower layer conductive portion 6 are contacted at points B, respectively. At this time, a conducting path (shown by a dotted line in FIG. 3(b)) between the upper layer conductive portion 4 and the lower layer conductive portion 6 has a length L'. This length L' becomes shorter than the length L while the pressure F is not applied. In a case where the pressure F applied to the upper layer conductive portion 4a is higher, the upper layer conductive portion 4 is curved downward further, and the conducting path has a length L". This length L" becomes shorter than the above-explained length L'. Therefore, the electric resistance R between the upper layer conductive portion 4 and the lower layer conductive portion 6 bears a proportionate relationship to the (electrically-effective) length (L', L") of the connecting yarn 8a, and becomes smaller when the pressure F applied to the upper layer conductive portion 4 becomes higher.

Although the lower layer conductive portion 6a is explained above, electric resistance R varies similarly with respect to the other lower layer conductive portions 6b, 6c . . . . Therefore, electric resistances R can be detected for all combinations of the upper layer conductive portions 4a, 4b, 4c . . . and the lower layer conductive portions 6a, 6b, 6c . . . , respectively.

Therefore, the applied pressure F and the electric resistance R between the upper layer conductive portion 4 and the lower layer conductive portion 6 vary continuously as shown in FIG. 4. Thus, the pressure F can be calculated from the electric resistance R, and thereby the variable resistor layer 8 has a pressure detection function. Since the upper layer 2, the lower layer 3 and the variable resistor layer 8 have air ventilation characteristic and the variable resistor layer 8 has a pressure detection function as explained above, the sheet pressure sensor 1 can detect the pressure F applied to the upper layer conductive portion(s) 4 or the lower layer conductive portion(s) 6 while keeping air ventilation characteristic. Here, it is possible in the present embodiment to detect a position on the sheet pressure sensor 1 to which the pressure F is applied in a grid pattern based on a combination position of the upper layer conductive portions 4a, 4b, 4c . . . and the lower layer conductive portions 6a, 6b, 6c . . . and the electric resistance R at the combination position.

In a sheet pressure sensor 1 according to a third embodiment, as a connecting yarn(s) 8a, used is a conductive polymer fiber(s) made by coating a pasting solution made by dispersing carbon black (manufactured by Mitsubishi Chemical Corporation) to PVA by 20 wt % on a polyester fiber(s) so that their cross-sectional area ratio becomes 50:50. Other configurations are the same as those in the first embodiment. Electric resistivity of the connecting yarn(s) 8a is 100 Ω·cm, and the same advantages as those brought in the first embodiment can be brought.

In a sheet pressure sensor 1 according to a fourth embodiment, a silver-coated fiber(s) (conductive polymer fiber(s)) is used as a connecting yarn(s) 8a. The silver-coated fiber(s) is configured by coating silver on a surface of a polyester fiber(s). Other configurations are the same as those in the first embodiment. Electric resistivity of the connecting yarn(s) 8a is 0.01 Ω·cm, and the same advantages as those brought in the first embodiment can be brought.

In a sheet pressure sensor 1 according to a fifth embodiment, as a connecting yarn(s) 8a, used is a conductive polymer fiber(s) made by coating a pasting solution made by dispersing zinc oxide (ZnO) to PVA by 20 wt % on a polyester fiber(s) so that their cross-sectional area ratio becomes 50:50. Other configurations are the same as those in the first embodiment. Electric resistivity of the connecting yarn(s) 8a is 10 Ω·cm, and the same advantages as those brought in the first embodiment can be brought.

In a sheet pressure sensor 1 according to a sixth embodiment, as a connecting yarn(s) 8a, used is a conductive polymer fiber(s) made by coating aqueous dispersion of PEDOT/PSS on a polyester fiber(s) so that their cross-sectional area ratio becomes 50:50. Other configurations are the same as those in the first embodiment. Electric resistivity of the connecting yarn(s) 8a is 1 Ω·cm, and the same advantages as those brought in the first embodiment can be brought.

In a sheet pressure sensor 1 according to a seventh embodiment, as a connecting yarn(s) 8a, used is a conductive polymer fiber(s) made by a wet-spinning method using a 5% aqueous solution of conductive polymer polypyrrol and having a 10 μm diameter. Electric resistivity of the connecting yarn(s) 8a is 1 Ω·cm, and the same advantages as those brought in the first embodiment can be brought.

Figure 8:
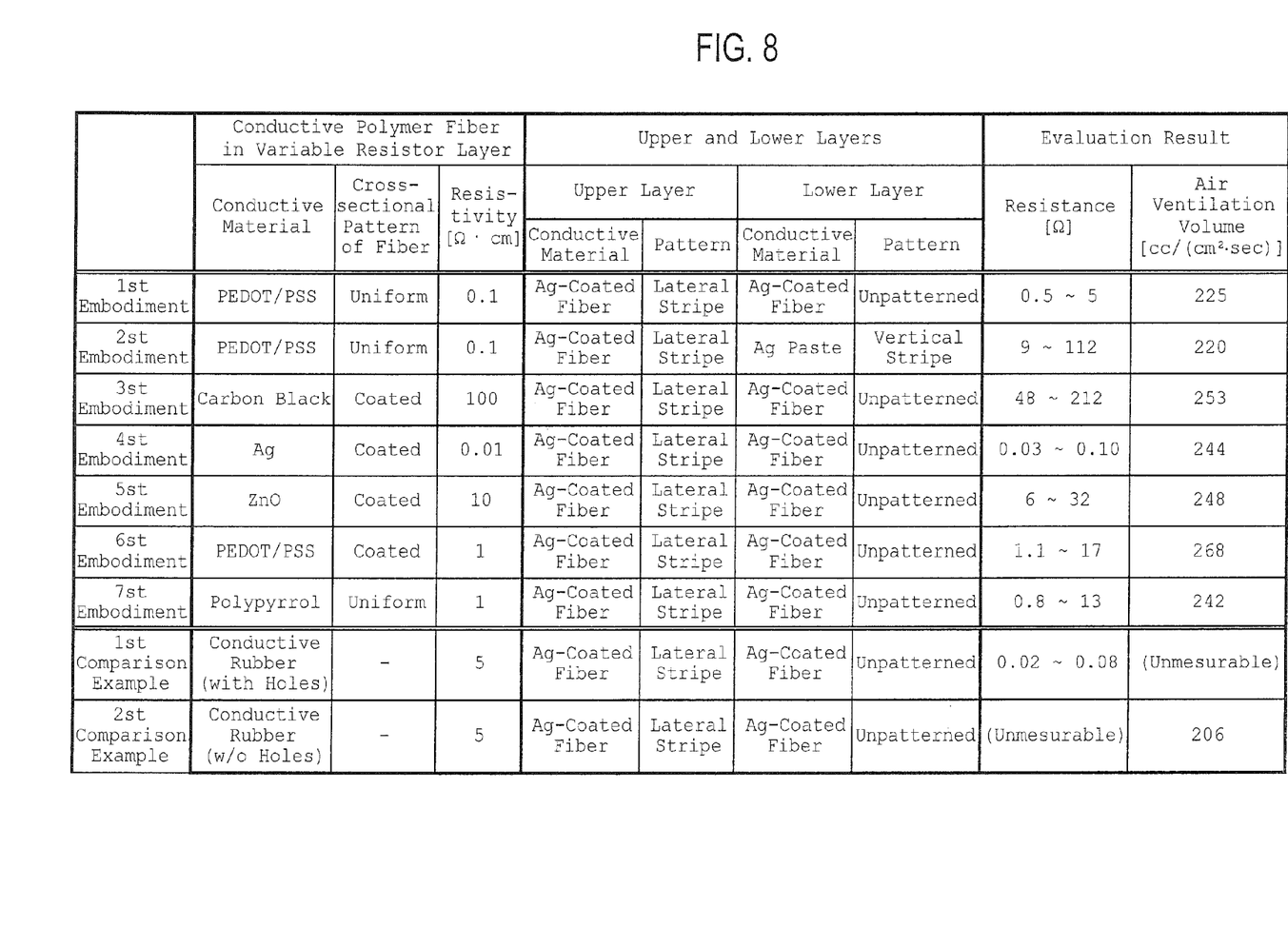
FIG. 8 is a table showing specifications and evaluation results of the embodiments and comparative examples.

Evaluation results of the first to seventh embodiments are presented in a table shown in FIG. 8. In first and second comparison examples in the table, a conductive rubber sheet is used instead of the variable resistor layer 8. Their configurations of the upper layer 2 and the lower layer 3 are the same as those in the first embodiment. As understood from the table, the embodiments have appropriate ranges for detecting electric resistance, but electric resistance ranges of the comparative examples are narrow (or unmeasurable) and thereby accurate detection may not be done. In addition, the embodiments provide sufficient air ventilation volumes, but air ventilation volumes of the comparative examples are small (or unmeasurable: no air ventilation) and thereby comfortability is not good.

As a conductive material, adopted can be a wire(s) made of metal such as gold, silver, copper and Nichrome, a carbon-based material such as carbon graphite, a particulate material made of semiconductor such as metallic oxide or metal, and a conductive polymer material such as acetylene series, complex 5-men circle system, phenylene series and aniline series. As the carbon-based material, used can be a fiber(s) made by spinning with mixture of carbon fibers, carbon powders and so on, in addition to commonly marketed products such as carbon fiber (manufactured by Toray Industries, Inc.: Torayca (registered trademark), by Osaka Gas Chemicals Co., Ltd.: Donacarbo, and so on). As the particulate material, used can be carbon powders such as carbon black (manufactured by Lion Corporation: Ketjenblack), and microparticles made of metal such as iron and aluminum. In addition, microparticles made of semiconductor such as tin oxide ($SnO_2$) and zinc oxide (ZnO) can be also used as the particulate material. Here, the conductive polymer fiber(s) refers to materials among the above conductive materials except metals.

Can be used materials formed uniformly by the above-mentioned conductive materials, materials coated by the above-mentioned conductive materials by vapor-deposition or pasting, and materials in which the above-mentioned conductive materials are used as a core material and its surface is coated by another material. In view of availability, specific weight and so on, it is preferable to use carbon fibers or carbon powders as the conductive material. In addition, the conductive material may be made of a single material, or plural materials.

It is preferable that the upper layer 2 is made of fibers for air ventilation characteristic. Note that the upper layer conductive portion(s) 4 can be formed by pasting conductive paint on the upper layer 2 in a stripe manner or uniformly on an entire surface thereof. As the conductive paint, Dotite manufactured by Fujikura Kasei Co., Ltd. can be used. In order to avoid degradation of comfortability due to partial difference of hardness, a metallic wire(s) and a conductive fiber(s) (e.g. a twisted wire(s) made of metal such as nickel) that has an almost the same cross-sectional area as that of a fiber(s) forming the upper layer 2, the lower layer 3 and the variable resistor layer 8 can be used for the upper layer conductive portion(s) 4. The above is similarly applied to the lower layer 3 (the lower layer conductive portion(s) 6).

It is preferable in view of costs and practicality to use fibers made of general-purpose resin, by itself or by being mixed with others, for the upper layer non-conductive portion(s) 5 and the lower layer non-conductive portion(s) 7, e.g. polyamide such as nylon 6 and nylon 66, polyethylene terephthalate, polyethylene terephthalate including copolymerized component, polybutylene terephthalate, and polyacrylonitrile. In addition, it is sufficient that the upper layer 2 and the lower layer 3 have a sheet shape with air ventilation characteristic, but it is preferable, in view of heat-retention characteristics and fixture of the variable resistor layer 8, that they are formed by woven cloth, non-woven cloth or knitted fabric made of commonly-used fibers.

As the resistance measurement device (measuring instrument/measurement means) 15, a commonly-used resistance meter or an LCR meter can be used, and an instrument or a means that uses a method for measuring voltage difference with respect to a reference resistance by a voltmeter can be used. In addition, the above-mentioned instruments can be used by itself and/or by being combined with others.

The fiber(s) mentioned here refers to a fiber(s) made by a melt-spinning, wet-spinning, or electro-spinning method, a fiber(s) made by being separated away from a film so as to cut slits on it, and so on. A fiber(s) having almost a few μm to a few hundreds μm diameter or width is preferable in view of formation of woven fabric or knitted fabric (weaving or knitting easiness, softness as woven cloth or knitted cloth, handling easiness as cloth, and so on). By bundling dozens to thousands of the above fibers, it becomes easy to handle as fibers. Here, they may be twisted.

In a case of using metallic fibers instead of the conductive polymer fibers, since electric resistivity of metal is especially low, it is needed to use extremely thin metallic fibers or to make a distance between the upper and lower layers wider in order to improve detection capability by widening a variable range (dynamic range) of electric resistivity of the variable resistor layer. However, if thin metallic fibers are used, it becomes impossible to widen a variable range of electric resistivity in a narrow measurement target area. In addition, electric resistance hardly changes even when metallic fibers and surrounding other fibers are contacted with each other in a measurement target area, and thereby it is impossible to improve detection capability. Further, if a distance between the upper and lower layers is made wider, applied pressure cannot be supported due to softness of metallic fibers. Since non-conductive portions are subject to be formed when other non-conductive fibers are mixed in order to support the pressure, it becomes impossible to improve detection capability by widening a variable range of electric resistivity.

The conductive polymer fiber(s) mentioned here refers to a fiber(s) in which the above-explained conductive materials are dispersed-in or pasted-on polymer commonly-used as a fiber(s), a fiber(s) itself made of conductive polymer materials, and so on. A conductive polymer fiber(s) that uses semiconductor, conductive polymer or a carbon fiber(s) as a conductive material(s) is especially preferable. Composition volume of the conductive material(s) in the conductive polymer fiber(s) is preferably 0.5 to 30 vol %. If the composition volume is less than 0.5 vol %, a volume of the conductive material(s) is insufficient, and thereby performance cannot be improved in comparison with a non-composition fiber(s) and it is not preferable because only cost rise is brought. On the other hand, if the composition volume is more than 30 vol %, melt viscosity of polymer resin (matrix resin) mixed with a conductive material(s) increases, and thereby it is not preferable because spinnability drastically degrades.

It is preferable in view of costs and practicality to use fibers made of general-purpose resin, by itself or by being mixed with others, as matrix resin, e.g. polyamide such as nylon 6 and nylon 66, polyethylene terephthalate, polybutylene terephthalate, and polyacrylonitrile. It is also preferable that the conductive polymer fiber(s) is coated by another polymer material(s).

When coating a conductive material on a polymer fiber, the above-explained electrical contacts (see the contact points B shown in FIG. 3(b)) can be easily obtained because the conductive material exists on a surface of the conductive polymer fiber, and thereby it becomes possible to widen the above-mentioned dynamic range. It is sufficient that a coating amount of the conductive material is in a range that doesn't inhibit detection capability, but it is preferable that the conductive material occupies not-less-than 10% and not-more-than 80% in a gross cross-sectional area (100%) of the conductive polymer fiber, and it is especially preferable that it occupies not-less-than 20% and not-more-than 50%.

Figure 7:
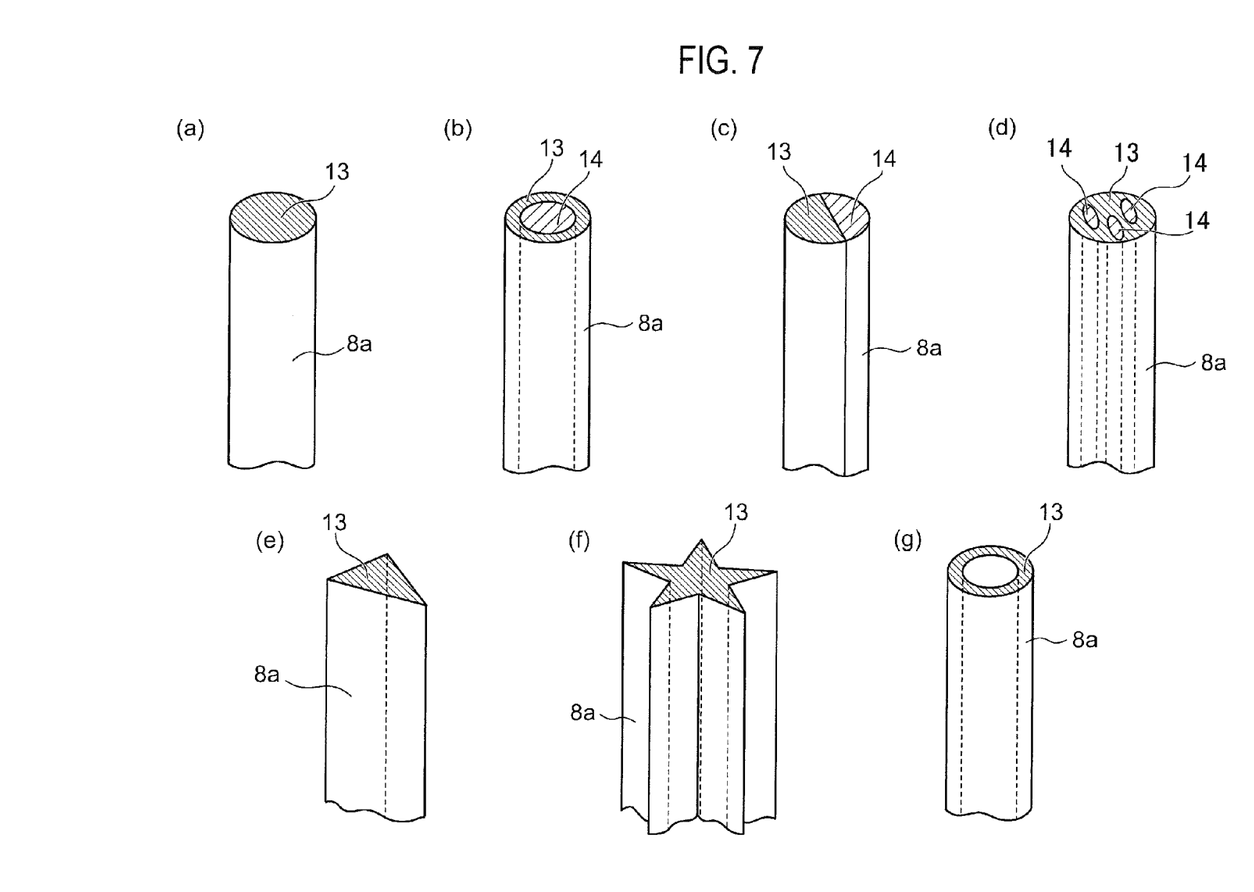
FIG. 7 are enlarged perspective view of conductive polymer fibers, and (a) shows the fiber made of a single material, (b) shows the fiber having a core-sleeve structure, (c) shows the fiber having a side-by-side structure, (d) shows the fiber having a sea-island (multi core) structure, (e) shows the fiber having a triangle cross-sectional shape, (f) shows the fiber having an astral cross-sectional shape and (g) shows the fiber having a hollow structure.

As shown in FIG. 7(a) to FIG. 7(g), it is preferable that various cross-sectional shapes and various cross-sectional structures are given to the conductive polymer fiber (the connecting yarn 8a) at its formation state or at its weaving/kitting stage after its fiberization. The conductive polymer fiber (the connecting yarn 8a) can have various cross-sections formed by a conductive portion(s) 13 and a non-conductive portion(s) 14. As shown in FIG. 7(a), the connecting yarn 8a may be formed uniformly by a conductive polymer material to have a general circular cross-sectional shape. As shown in FIG. 7(b), the connecting yarn 8a may have a core-sleeve structure. As shown in FIG. 7(c), the connecting yarn 8a may have a side-by-side structure. As shown in FIG. 7(d), the connecting yarn 8a may have a sea-island (multi core) structure. As shown in FIG. 7(e) and FIG. 7(f), the connecting yarn 8a may have a non-circular cross-sectional shape. As shown in FIG. 7(g), the connecting yarn 8a may have a hollow structure. These structures change static properties of the fibers. For example, the fibers themselves may quirk naturally according to the above-mentioned combination of different materials (the conductive portion 13 and the non-conductive portion 14) or types of cross-sectional shapes, so that it becomes possible to generate changes in textures. In addition, when a surface area of the fiber becomes large, it becomes possible to improve light-weighting property and heat-resistant property.

Further, the conductive polymer fiber (the connecting yarn 8a) also possesses heat-generation property due to its electric resistance. As in the above embodiments, when the sheet pressure sensor 1 including the conductive polymer fibers (the connecting yarns 8a) is used for a seat for an automobile, the sheet pressure sensor 1 also functions as a seat heater. Therefore, it becomes possible to achieve the above-explained pressure detection function, while exercising ingenuity in structures and materials of the fibers, in order to improve the heat-generation function in addition to the above-mentioned changes of static properties.

In order to achieve the above-explained pressure detection function, it is preferable that the electric resistivity of the conductive material is not-smaller-than $10^{-3}$ Ω·cm and not-larger-than $10^2$ Ω·cm. Namely, in a case where the conductive polymer fiber is formed uniformly by the conductive material, it is preferable that its electric resistivity is not-smaller-than $10^{-3}$ Ω·cm and not-larger-than $10^2$ Ω·cm. Since the conductive polymer fibers made into woven material or knitted material act as resistive elements, it becomes impossible to detect pressure accurately due to affection by contact resistance at the conduction portions (see the contact points B shown in FIG. 3(b)) when the resistance of the conductive material is too small (smaller than $10^{-3}$ Ω·cm). On the other hand, when the resistance of the conductive material is too large (larger than $10^2$ Ω·cm), electric current for detecting pressure becomes difficult to flow, and thereby it becomes impossible to get sufficient response. In addition, it is more preferable that the electric resistivity is not-smaller-than $10^{-2}$ Ω·cm and not-larger-than $10^1$ Ω·cm, and the above-mentioned heat generation function can be achieved efficiently by this range.

As the conductive polymer material (the conductive material) having the above-mentioned preferable electric resistivity, it is further preferable that it includes at least one of polypyrrol, PEDOT/PSS, polyaniline, and polyparaphenylene vinylene [PPV]. Furthermore, among the above materials, PEDOT/PSS (manufactured by Heraeus GmbH: Clevious P) that is made by doping poly-4-stylenesulfonate (PSS) to poly-3,4-ethylenedioxythiophene (PEDOT) that is conductive polymer of thiophene series, PPV that is one of phenylene series, polypyrrol that is one of pyrrol series, or the like are preferable, because they are easily-available as fibers.

The above-mentioned conductive polymer materials can be easily fiberized by a wet-spinning or electro-spinning method, and are preferable because they satisfy the above-explained electric resistivity. For example, materials of thiophene series, pyrrol series or aniline series can be easily fiberized by a wet-spinning Aqueous dispersion of PEDOT/PSS (manufactured by Heraeus GmbH: Clevious P) can be easily fiberized as a conductive polymer fiber by being extruded into acetone from a cylinder.

Figure 6:
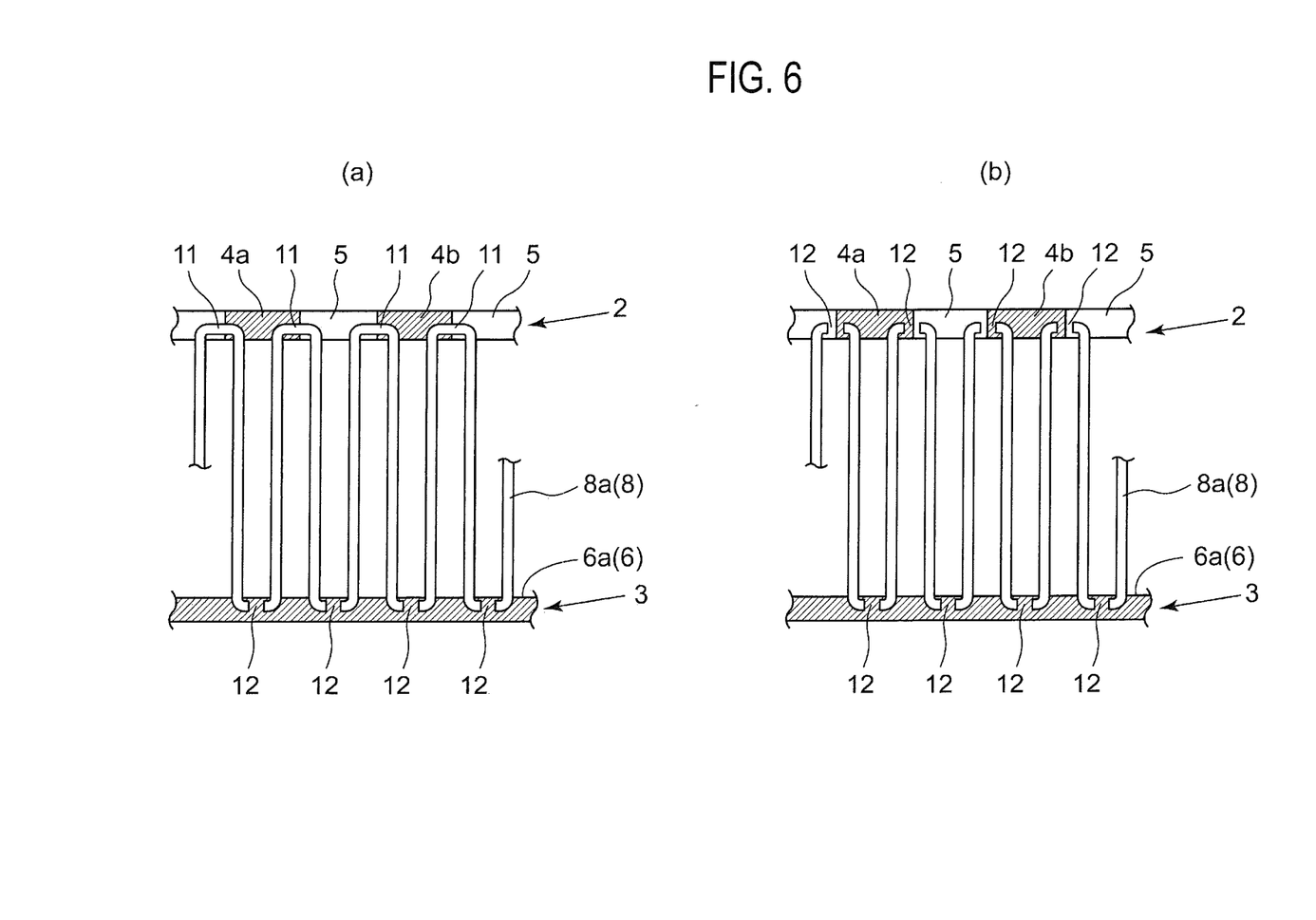
FIG. 6 is a cross-sectional view of modified examples of connecting yarns, and (a) shows a first modified example and (b) shows a second modified example.

By adopting the above-mentioned processes, the conductive polymer fibers for forming the sheet pressure sensor can be easily manufactured. Note that the connecting yarn(s) 8a is not necessarily continued as one string at its connecting portion(s) 11 (see FIG. 3(a) and FIG. 3(b)), but may be cut in one (or both) of the upper layer 2 and the lower layer 3 as shown in FIG. 6(a) and FIG. 6(b). However, in this case, a cut portion(s) 12 of the connecting yarn(s) 8a is needed to be fixed with the upper layer 2 or the lower layer 3 by some sort of methods or structures.

The entire contents of Japanese Patent Applications 2012-28118 (filed Feb. 13, 2012) are incorporated to this Specification by reference. Although the invention has been described above by reference to certain embodiments of the invention, the invention is not limited to the embodiments described above. Scope of the invention should be defined in view of Claims.

For example, the sheet pressure sensor can be applied not only to a seat for an automobile, but also to various usages such as a cover of a cushion and an electric carpet.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A sheet pressure sensor comprising:
   a first fiber layer that has a plurality of first conductive portions having conductivity, and a plurality of first non-conductive portions electrically insulating the plurality of first conductive portions, respectively;
   a second fiber layer that is disposed oppositely to the first fiber layer and distanced away from the first fiber layer, and has a second conductive portion having conductivity;
   a third fiber layer that is provided between the first fiber layer and the second fiber layer; and
   a measuring instrument that measures electric resistance between the plurality of first conductive portions and the second conductive portion,
   wherein the third fiber layer is configured of a plurality of connecting yarns that is extended from one of the plurality of first conductive portions and the second conductive portion to another thereof to connect the plurality of first conductive portions and the second conductive portion,
   wherein the plurality of connecting yarns further electrically connects the plurality of first conductive portions and the second conductive portion with a predetermined electric resistivity, respectively,
   wherein, when the first fiber layer or the second fiber layer is deformed by pressure application, a connecting yarn near the pressure application among the plurality of connecting yarns deforms due to deformation of the first fiber layer or the second fiber layer, and shortens a length of a conducting path formed by the connecting yarn between the plurality of first conductive portions and the second conductive portion to reduce electric resistance between the plurality of first conductive portions and the second conductive portion,
   wherein each of the plurality of connecting yarns has a first end thereof embedded in the first fiber layer, and a second end thereof embedded in the second fiber layer,
   wherein the plurality of connecting yarns have ventilation gaps therebetween, and
   wherein an outer surface of each of the plurality of connecting yarns has electrical conductivity.

2. The sheet pressure sensor according to claim 1,
   wherein the second fiber layer has the second conductive portion in a plurality, and a plurality of second non-conductive portions electrically insulating the plurality of second conductive portions, respectively,
   wherein the plurality of second conductive portions is connected with the first conductive portions by the plurality of connecting yarns, and
   wherein the plurality of connecting yarns further electrically connects the plurality of first conductive portions and the plurality of second conductive portions with the predetermined electric resistivity, respectively.

3. The sheet pressure sensor according to claim 1,
   wherein the plurality of connecting yarns is formed of conductive polymer fibers.

4. The sheet pressure sensor according to claim 3,
   wherein the conductive polymer fibers contain semi-conductive polymer.

5. The sheet pressure sensor according to claim 3,
   wherein the conductive polymer fibers contain carbon.

6. The sheet pressure sensor according to claim 3,
   wherein the conductive polymer fibers are configured by coating conductive materials on surfaces of fibers.

7. The sheet pressure sensor according to claim 3,
   wherein electric resistivity of the conductive polymer fibers is not-smaller-than $10^{-3}$ $\Omega \cdot cm$ and not-larger-than $10^{2}$ $\Omega \cdot cm$.

8. A sheet pressure sensor comprising:
   a first fiber layer that has a plurality of first conductive portions having conductivity, and a plurality of first non-conductive portions electrically insulating the plurality of first conductive portions, respectively;
   a second fiber layer that is disposed oppositely to the first fiber layer and distanced away from the first fiber layer, and has a second conductive portion having conductivity;
   a third fiber layer that is provided between the first fiber layer and the second fiber layer; and
   a measurement means for measuring electric resistance between the plurality of first conductive portions and the second conductive portion,
   wherein the third fiber layer is configured of a plurality of connecting yarns that is extended from one of the plurality of first conductive portions and the second conductive portion to another thereof to connect the plurality of first conductive portions and the second conductive portion,
   wherein the plurality of connecting yarns further electrically connects the plurality of first conductive portions and the second conductive portion with a predetermined electric resistivity, respectively,
   wherein, when the first fiber layer or the second fiber layer is deformed by pressure application, a connecting yarn near the pressure application among the plurality of connecting yarns deforms due to deformation of the first fiber layer or the second fiber layer, and shortens a length of a conducting path formed by the connecting yarn between the plurality of first conductive portions and the second conductive portion to reduce electric resistance between the plurality of first conductive portions and the second conductive portion,
   wherein each of the plurality of connecting yarns has a first end thereof embedded in the first fiber layer, and a second end thereof embedded in the second fiber layer,
   wherein the plurality of connecting yarns have ventilation gaps therebetween, and
   wherein an outer surface of each of the plurality of connecting yarns has electrical conductivity.

9. The sheet pressure sensor according to claim 8,
   wherein the measurement means detects pressure of the pressure application based on a change of the electric resistance due to the short-circuit.

* * * * *